US012778986B2

(12) United States Patent
Carter et al.

(10) Patent No.: US 12,778,986 B2
(45) Date of Patent: Nov. 3, 2026

(54) BONE DERIVED FIBERS AND OXYGENATED WOUND TREATMENTS

(71) Applicant: TETROUS, INC., Sherman Oaks, CA (US)

(72) Inventors: Andrew J. Carter, June Lake, CA (US); Bradley E. Patt, Sherman Oaks, CA (US); Nelson L. Scarborough, Andover, MA (US)

(73) Assignee: TETROUS, INC., Sherman Oaks, CA (US)

( * ) Notice: Subject to any disclaimer, the term of this patent is extended or adjusted under 35 U.S.C. 154(b) by 0 days.

(21) Appl. No.: 19/313,529

(22) Filed: Aug. 28, 2025

(65) Prior Publication Data

US 2025/0381232 A1 Dec. 18, 2025

Related U.S. Application Data

(63) Continuation of application No. 18/132,087, filed on Apr. 7, 2023, now Pat. No. 12,419,916, which is a continuation of application No. 17/327,554, filed on May 21, 2021, now Pat. No. 11,622,979, which is a continuation of application No. 16/316,968, filed as application No. PCT/US2017/041574 on Jul. 11, 2017, now Pat. No. 11,045,499.

(60) Provisional application No. 62/360,652, filed on Jul. 11, 2016.

(51) Int. Cl.

| | |
|---|---|
| ***A61K 35/32*** | (2015.01) |
| ***A61K 9/00*** | (2006.01) |
| ***A61K 9/06*** | (2006.01) |
| ***A61K 9/70*** | (2006.01) |
| ***A61L 27/36*** | (2006.01) |
| ***A61L 27/44*** | (2006.01) |
| ***A61L 27/46*** | (2006.01) |
| ***A61L 27/50*** | (2006.01) |

(52) U.S. Cl.

CPC ............ *A61K 35/32* (2013.01); *A61K 9/0014* (2013.01); *A61K 9/06* (2013.01); *A61K 9/7007* (2013.01); *A61L 27/3612* (2013.01); *A61L 27/365* (2013.01); *A61L 27/446* (2013.01); *A61L 27/46* (2013.01); *A61L 27/50* (2013.01); *A61L 2430/02* (2013.01)

(58) Field of Classification Search

None

See application file for complete search history.

(56) References Cited

U.S. PATENT DOCUMENTS

| | | | | |
|---|---|---|---|---|
| 11,045,499 | B2 * | 6/2021 | Carter | A61L 27/46 |
| 11,622,979 | B2 * | 4/2023 | Carter | A61L 27/46<br>424/94.67 |
| 12,419,916 | B2 * | 9/2025 | Carter | A61K 9/0014 |
| 2004/0224406 | A1 | 11/2004 | Altman et al. | |
| 2007/0191963 | A1 | 8/2007 | Winterbottom et al. | |
| 2008/0091270 | A1 | 4/2008 | Miller et al. | |
| 2014/0314882 | A1 | 10/2014 | Carter et al. | |
| 2015/0004247 | A1 | 1/2015 | Carter et al. | |
| 2015/0093429 | A1 | 4/2015 | Carter et al. | |
| 2015/0283182 | A1 | 10/2015 | Guelcher et al. | |
| 2015/0306278 | A1 | 10/2015 | McKay | |
| 2016/0081803 | A1 | 3/2016 | McKay | |

OTHER PUBLICATIONS

Edwards et al.; "Osteoinduction of Human Demineralized Bone: Characterization in a Rat Model"; Clin Orthop Rel Res; 357; 1998; pp. 219-228.

Isaacson et al.; "Tourniquet use in combat-injured service members: a link with heterotopic ossification?"; Orthopedic Research and Reviews; 6; 2014; pp. 27-31.

Rendl et al.; "BMP signaling in dermal papilla cells is required for their hair follicle-inductive properties"; Genes & Development; 22(4); 2008; pp. 543-557.

* cited by examiner

*Primary Examiner* — Blaine Lankford

(74) *Attorney, Agent, or Firm* — Squire Patton Boggs (US) LLP

(57) ABSTRACT

A composition for the treatment of wounds includes demineralized bone fibers (DBF) derived from allogeneic or xenogenic cortical bone and/or polymeric fibers made from resorbable and/or non-resorbable polymer, and the composition may also include an oxygen-generating material and/or an oxygen carrier.

9 Claims, 4 Drawing Sheets

BONE DERIVED FIBERS AND OXYGENATED WOUND TREATMENTS

CROSS-REFERENCE TO RELATED APPLICATION(S)

This application is a continuation of U.S. application Ser. No. 18/132,087, filed Apr. 7, 2023, which is a continuation of U.S. application Ser. No. 17/327,554 filed on May 21, 2021 (issued as U.S. Pat. No. 11,622,979), which is a continuation of U.S. application Ser. No. 16/316,968 filed on Jan. 10, 2019, (issued as U.S. Pat. No. 11,045,499 on Jun. 29, 2021) which is a national entry of WO PCT/US2017/041574 filed on Jul. 11, 2017, which claims the benefit of U.S. application Ser. No. 62/360,652 filed on Jul. 11, 2016. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

STATEMENT REGARDING FEDERALLY SPONSORED RESEARCH OR DEVELOPMENT

This invention was made with government support under 1R43NR017127-01A1 awarded by the National Institute of Nursing Research (NINR). The government has certain rights in the invention.

FIELD

The present invention generally relates to devices used in wound care, and in particular to the healing of wounds where vascularization is compromised.

BACKGROUND

It has been estimated that about 26 million patients suffer from chronic wounds each year. Chronic wounds include diabetic foot ulcers, venous stasis ulcers, pressure ulcers, burns, and surgical wounds. Those at highest risk for developing chronic wounds include patients with diabetes, disabilities, and the elderly. These patients suffer not only from the physical pain of the wound, but also from stress and a poor quality of life.

Standard treatment for chronic wounds usually involves cleaning the wound, debriding the wound, and applying a dressing to maintain a moist tissue environment conducive to healing. In many cases, treatment also includes the use of antibiotics since chronic wounds are also frequently infected. Antibiotics may be administered systemically and/or by using a dressing containing an antibiotic.

Clinicians will also try to eliminate underlying factors that cause the formation of chronic wounds.

Unfortunately, a significant number of patients with chronic wounds are not healed after 3 months, 6 months, or even after one year of treatment. In the worst cases, amputation may be necessary, and elderly patients may even develop sepsis and die.

There are a number of reasons why chronic wounds are difficult to heal. One reason is the lack of or delay in new blood vessel formation that is necessary to provide oxygen to support newly deposited tissue during the wound healing process. A second reason is the lack of an adequate scaffold to support formation of a repair tissue.

Research on the formation of new Extracellular Matrix (ECM) in chronic wounds has led to the development, for example, of products like Promogran Prisma™ by Acelity (formerly Systagenix) which incorporates oxidized regenerated cellulose (ORC). The ORC inhibits proteases in chronic wounds that are considered to be detrimental to the formation of new ECM in order to improve wound healing.

Clinicians have also experimented with the use of autologous wound healing factors, derived from a patient's blood, to improve wound healing. For example, the topical application of platelet-derived growth factor (PDGF) has been investigated in the clinic. Studies have also evaluated the use of autologous platelet-rich plasma (PRP) in the healing of chronic wounds. McNeil Pharmaceutical has also introduced a recombinant PDGF product, Regranex™ Gel, to heal diabetic ulcers. Unfortunately, in 2008 the manufacturer added a warning to the product noting that an increased incidence of mortality secondary to malignancy was observed when patients were treated with three or more tubes of the Regranex™ Gel in a post-market retrospective cohort study.

Accordingly, there is a need for devices, such as implants and dressings, with increased oxygen content to stimulate the healing of chronic as well as acute wounds.

SUMMARY

Some embodiments of the present invention include improved devices, such as dressings and implants, for treating wounds. Some embodiments of the present invention include processes for making such devices.

Some embodiments of the present invention include improved methods for treating wounds. For example the methods are disclosed for treating chronic and/or acute wounds.

Embodiments of the present invention include devices, such as dressings and implants, for the treatment of chronic or acute wounds that are derived from demineralized bone fibers. In some embodiments, the devices include an oxygen carrier or a source of oxygen that is particularly useful when it is desirable to compensate for a lack of effective blood flow in a region such as in a chronic wound. In some embodiments, the implants are resorbable; provide a temporary scaffold for the in-growth of cells, tissues, and blood vessels to help regenerate the extracellular matrix; and deliver oxygen to the chronic wound. The dressings and implants may also include antibiotics for the treatment or prevention of infection in the wound.

The devices allow delivery of oxygen to the wound in a controlled manner for a prolonged period of time. In some embodiments, the devices are made from extra cellular matrix-derived materials. In some embodiments, devices made from ECM-derived materials may also include polymeric compositions, creams, and/or gels. The oxygenated cream or gel may be incorporated into the dressing or may be added at the time of initial dressing application. The oxygenated cream or gel may be applied at regular intervals, for example, daily, during the wound healing process. The extra cellular matrix derived materials may include fibers derived from demineralized bone. Additionally, the demineralized bone may be treated to remove bone morphogenic proteins (BMPs). The bone may be allogenic or xenogenic. The xenogenic materials may be treated to reduce their immunological potential. The polymeric compositions include but are not limited to, resorbable polymers.

According to some embodiments of the present invention, dressings may have a film laminated to the upper surface or a cover film dressing to act as a barrier to prevent oxygen and/or moisture loss from the treatment into the atmosphere. In other embodiments of the present invention, dressings are used in conjunction with an adhesive film dressing such as Opsite (Smith & Nephew) or Tegaderm™ (3M).

In some embodiments of the present invention, a composition for the treatment of wounds, includes demineralized bone fibers (DBF) derived from allogeneic or xenogenic cortical bone.

In some embodiments of the present invention, a composition for the treatment of wounds includes polymeric fibers made from resorbable and/or non-resorbable polymer.

In some embodiments of the present invention, a composition for the treatment of wounds includes DBF fibers and polymeric fibers made from resorbable and/or non-resorbable polymers.

In some embodiments of the present invention, a composition for the treatment of wounds includes DBF fibers and oxygen generating materials and/or an oxygen carrier. In some embodiments, the oxygen generating materials and/or the oxygen carrier is coated on the DBF or the polymeric fibers. In some embodiments of the present invention, the oxygen generating materials are selected from the group consisting of Calcium Peroxide, Magnesium Peroxide, Sodium Percarbonate, Sodium Peroxide, and mixtures thereof. In some embodiments, the oxygen carrier is a perfluorocarbon selected from perfluorodecalin, perfluorohexane, perfluoroperhydrophenanthrene, perfluorobutylamine (PFTBA or PFTBM), perfluorooctylbromide (PFOB), perfluoro-n-octane, octafluoropropane, perfluorodichlorooctane, perfluorodecalin (PFD), perfluorotripropylamine, perfluorotrimethylcyclohexane, perfluoromethyladamantane, perfluorodimethyladamantane, perfluoromethyldecaline, perfluorofluorene, diphenyldimethylsiloxane, hydrogen-rich monohydroperfluorooctane, alumina-treated perfluorooctane, or mixtures thereof.

In some embodiments of the present invention, a composition for the treatment of wounds includes polymeric fibers made from resorbable and/or non-resorbable polymer, where the non-resorbable polymer is selected from poly(ethylene), poly(propylene), poly(tetrafluoroethylene), poly(methacrylates), poly(methylmethacrylate), ethylene-co-vinylacetate, poly(dimethylsiloxane), poly(ether-urethanes), poly(ethylene terephthalate), nylon, polyurethane, poly(sulphone), poly(aryletherketone), poly(ethyleneoxide), poly(ethyleneoxide-co-propyleneoxide), poly(vinylpyrrolidine), poly(vinylalcohol), or combinations thereof.

In some embodiments of the present invention, a composition for the treatment of wounds includes polymeric fibers made from resorbable and/or non-resorbable polymer, where the non-resorbable polymer is selected from proteins, peptides, silk, collagen, polysaccharides, resorbable polyesters, including resorbable polyesters made from hydroxy acids, resorbable polyesters made from diols and diacids; polycarbonates; tyrosine polycarbonates, natural and synthetic polyamides, natural and synthetic polypeptides, natural and synthetic polyaminoacids, polyesteramides, poly(alkylene alkylates), polyethers, polyvinyl pyrrolidones, polyurethanes, polyetheresters, polyacetals, polycyanoacrylates, poly(oxyethylene)/poly(oxypropylene) copolymers, polyacetals, polyketals, polyphosphates, (phosphorous-containing) polymers, polyphosphoesters, polyalkylene oxalates, polyalkylene succinates, poly(maleic acids), biocompatible copolymers, hydrophilic or water soluble polymers, or combinations thereof.

In some embodiments of the present invention, a composition for the treatment of wounds includes polymeric fibers made from collagen, where the collagen is selected from Types I, II, III, IV, V or combinations thereof.

In some embodiments of the present invention, a composition for the treatment of wounds includes polymeric fibers made from proteins or peptides, wherein the proteins or peptides include one or more of alanine, arginine, asparagine, aspartic acid, cysteine, glutamine, glutamic acid, glycine, histidine, isoleucine, lysine, methionine, phenylalanine, proline, serine, threonine, tryptophan, tyrosine and valine.

In some embodiments of the present invention, a composition for the treatment of wounds includes polymeric fibers made from polysaccharides, where the polysacchardies are selected from alginate, amylose, carboxymethylcellulose, cellulose, chitin, chitosan, cyclodextrin, dextran, dextrin, gelatin, gellan, glucan, hemicellulose, hyaluronic acid, derivatized hyaluronic acid, oxidized cellulose, pectin, pullulan, sepharose, xanthan and xylan;

In some embodiments of the present invention, a composition for the treatment of wounds includes resorbable polyesters selected from poly(lactides), poly(glycolides), poly(lactide-co-glycolides), poly(lactic acid), poly(glycolic acid), poly(lactic acid-co-glycolic acid), poly(dioxanones), polycaprolactones and polyesters with one or more of the following monomeric units: glycolic, lactic; trimethylene carbonate, p-dioxanone, -caprolactone, and combinations thereof, and/or the polyethers are selected from polyethylene glycol (PEG) or polyethylene oxide (PEO), and/or the biocompatible copolymers are selected from polyethylene (PEG) or (PVP) with a block of a different biocompatible or biodegradable polymers selected from poly(lactide), poly(lactide-co-glycolide), polycaprolactone and combinations thereof.

In some embodiments of the present invention, a composition for the treatment of wounds includes a film layer on the surface of the composition that does not contact the wound. In some embodiments, the film layer is a laminate film layer that is laminated to the DBF and/or polymeric fibers. In some embodiments, the film layer is made of polyurethane, ethylene vinyl alcohol, or silicone.

In some embodiments of the present invention, a composition for the treatment of wounds includes a bioactive agent selected from butyric acid, growth factors, inhibitors of matrix metalloproteinases (MMPs), retinols, antioxidants, antibiotics, biofilm inhibitors, vitamins, anti-inflammatory drugs, lipids, steroids, hormones, antibodies, proteins, peptides, glycoproteins, signaling ligands, platelet rich plasma, amniotic membrane materials, anti-septic agents, analgesics, anesthetics, immunomodulatory agents, and molecules that promote the formation of extra cellular matrix (ECM), vascularization, and wound healing.

In some embodiments of the present invention, a composition for the treatment of wounds includes an antibiotic selected from bacitracin, neomycin, polymixin B, zinc, fusidic acid, gentamicin, mafenide acetate, metronidazole, minocycline, mupirocin, nitrofurazone, polymixin, retapamulin, rifampin, silver particles, silver sulfadiazine, sulfacetamide, vancomycin, and combinations thereof.

In some embodiments of the present invention, a composition for the treatment of wounds includes DBF that has been treated to remove bone morphogenic proteins (BMPs) and/or antigenic proteins. In some embodiments, the DBF is treated with a chaotropic agent. In some embodiments, the DBF is treated with a protease.

In some embodiments of the present invention, a method of producing a composition for treating wounds includes preparing a sheet of demineralized bone fibers from cortical bone and/or polymeric fibers. In some embodiments, the method also includes coating the sheet with an oxygen carrier and/or an oxygen generating material.

In some embodiments of the present invention, the method of producing a composition for treating wounds includes preparing a sheet of demineralized bone fibers from cortical bone and/or polymeric fibers and coating the sheet with an oxygen carrier and/or an oxygen generating material selected from Calcium Peroxide, Magnesium Peroxide, Sodium Percarbonate, Sodium Peroxide, or mixtures thereof.

In some embodiments of the present invention, the method of producing a composition for treating wounds includes preparing a sheet of demineralized bone fibers from cortical bone and/or polymeric fibers and coating the sheet with an oxygen carrier selected from perfluorodecalin, perfluorohexane, perfluoroperhydrophenanthrene, perfluorobutylamine (PFTBA or PFTBM), perfluorooctylbromide (PFOB), perfluoro-n-octane, octafluoropropane, perfluorodichlorooctane, perfluorodecalin (PFD), perfluorotripropylamine, perfluorotrimethylcyclohexane, perfluoromethyladamantane, perfluorodimethyladamantane, perfluoromethyldecaline, perfluorofluorene, diphenyldimethylsiloxane, hydrogen-rich monohydroperfluorooctane, alumina-treated perfluorooctane, or mixtures thereof.

In some embodiments of the present invention, the oxygen generating material and/or the perfluorocarbon is dispersed in a dispersing agent forming a cream, emulsion, or gel that is coated on the sheet. In some embodiments of the present invention, the dispersing agent is selected from glycerols, phospholipids, lecithins, surfactants, polyoxymers, or combinations thereof.

In some embodiments of the present invention, the method of producing a composition for treating wounds includes preparing a sheet of demineralized bone fibers from cortical bone and/or polymeric fibers, coating the sheet with an oxygen carrier and/or an oxygen generating material, and adhering a film layer to a surface of the sheet. In some embodiments of the present invention, the film layer is made of polyurethane, ethylene vinyl alcohol, or silicone.

In some embodiments of the present invention, a method of treating a wound in a subject having a wound, includes administering the composition as disclosed in any embodiment of the present invention. In some embodiments, the method also includes administering a cream, emulsion, or gel comprising an oxygen generator or a perfluorocarbon to the composition before or after the administering of the composition to the subject. In some embodiments, the administering of the cream, emulsion, or gel includes reapplication of the cream, emulsion, or gel on a daily, every other day, every third day, twice a week, or weekly basis.

DETAILED DESCRIPTION

Figure 1:
FIG. 1 shows a "ball" of demineralized bone fibers (DBF) according to embodiments of the present invention that can be used as a "free form" dressing to pack an irregular shaped wound; in which the fibers are optionally coated with an oxygen carrier material.

Embodiments of the present invention include devices and methods for supporting the formation of new tissue at a wound site of a subject by using technologies that increase the local oxygen concentration and may offset the effects of a lack of vascularity and the utility of using bone-derived fibers as a scaffold for tissue regeneration.

In some embodiments of the present invention, the oxygen carrier is a perfluorocarbon (PFC). These materials have a very high inherent solubility for oxygen. Non-limiting examples of PFCs include perfluorodecalin, perfluorohexane, perfluoroperhydrophenanthrene, perfluorobutylamine (PFTBA or PFTBM), perfluorooctylbromide (PFOB), perfluoro-n-octane, octafluoropropane, perfluorodichlorooctane, perfluorodecalin (PFD), perfluorotripropylamine, perfluorotrimethylcyclohexane, perfluoromethyladamantane, perfluorodimethyladamantane, perfluoromethyldecaline, perfluorofluorene, diphenyldimethylsiloxane, hydrogen-rich monohydroperfluorooctane, alumina-treated perfluorooctane, mixtures thereof, or any suitable oxygen carrier.

Perfluorocarbons are extremely hydrophobic materials and as such this property makes their incorporation into wound dressing materials very difficult. Embodiments of the present invention include means and/or methods by which perfluorocarbons are incorporated into wound dressing materials.

Some embodiments of the present invention include materials and methods through which oxygen may be generated in the applied dressing. For example, calcium peroxide reacts with water to liberate oxygen. By encapsulation of oxygen-producing or oxygen-enriching materials in a resorbable polymer matrix the rate of evolution of oxygen may be controlled.

In other embodiments of the present invention, an extracellular matrix (ECM), may be derived from demineralized bone that has utility in wound healing. In some embodiments, the ECM is made from collagen alone or collagen is the most abundant component. This ECM provides a matrix that supports proliferation and migration of cells, and may be used on its own, or may incorporate oxygenated or oxygen-generating materials, resulting in a template for accelerated tissue healing.

It has been shown that demineralized bone matrix (DBM) placed into a soft tissue site will stimulate bone formation. Indeed the osteoinductivity of DBM is measured by placing DBM in an intermuscular pouch in athymic rats and evaluating bone formation as disclosed in Edwards, Diegmann, and Scarborough; Clin Orthop Rel Res 357, 219-28, 1998, the entire content of which is incorporate by reference. Accordingly, it was surprising to observe that fibers made from demineralized bone matrix according to embodiments of the present invention were effective at stimulating soft tissue (i.e., non-bone) healing. As described below, there was some transient bone formation observed, however, surprisingly, good soft tissue healing was stimulated by the dressing. These isolated, small islands of apparent bone formation activity also appeared to be resorbing. Without being bound by any theory, it is possible that the absence of mechanical loading on the new bone provides signaling to the bone-like cells to resorb, as described by Wolff's Law, which states that bone in a healthy person or animal will adapt to the loads under which it is placed.

Bone morphogenic proteins (BMPs) have been identified as important in the signaling of dermal papilla cells to induce hair follicle induction as disclosed in Rendl et al. (Rendl, M., Polak, L. and Fuchs, E., 2008. BMP signaling in dermal papilla cells is required for their hair follicle-inductive properties, Genes & Development, 22(4), pp. 543-557 the entire content of which is herein incorporated by reference). Accordingly, there may be particular utility in the use of dressings according to embodiments of the present invention for use in wounds where subsequent hair production is required or desired.

Methods according to embodiments of the present invention allow for the controlled release of oxygen for the treatment of chronic and acute wounds. The devices according to embodiments of the present invention include dressings that temporarily cover a wound (and may be in contact with a wound) and are subsequently removed from the wound, implants that are applied to the wound and are not removed, or gels or creams. In all cases, the devices or means (e.g., dressings, implants, gels, or creams) are configured to continually dose the wound with oxygen to promote healing of the wound. When the device is an implant, it may be a resorbable implant that provides a temporary scaffold to promote regeneration of the ECM. The scaffolds allow and/or encourage in-growth of cells, tissues, and blood vessels to help regenerate the ECM, in addition to delivering oxygen to the chronic wound to stimulate and promote healing.

In the case of a wound resulting from an incision (i.e., an incisional wound), the oxygenated material in the form of a gel or emulsion may be applied to the incisional wound tissues prior to closure. A further oxygenated dressing may optionally be applied to the skin over the incision.

The resorbable implants may be made from resorbable synthetic or natural polymeric materials. In some embodiments of the present invention, the scaffolds of the resorbable implants are made from proteins, such as silk or collagen. In some embodiments, the fibers may be made from demineralized and/or devitalized bone. The bone may be allogeneic or xenogeneic.

Oxygen is delivered from the dressing by use of an oxygen carrier, a material that inherently has a high oxygen solubility. These materials may be directly coated or impregnated into the fibrous dressing material or may be incorporated into a gel or emulsion. In some embodiments, an oxygen carrier is directly coated on a dressing for utilization in resorbable dressings as it provides the means of incorporating the highest concentration of oxygen into the dressing.

In some embodiments, the oxygen carrier is a perfluorocarbon (PFC). Non-limiting examples of PFCs include perfluorodecalin, perfluorohexane, perfluoroperhydrophenanthrene, perfluorobutylamine (PFTBA or PFTBM), perfluorooctylbromide (PFOB), perfluoro-n-octane, octafluoropropane, perfluorodichlorooctane, perfluorodecalin (PFD), perfluorotripropylamine, perfluorotrimethylcyclohexane, perfluoromethyladamantane, perfluorodimethyladamantane, perfluoromethyldecaline, perfluorofluorene, diphenyldimethylsiloxane, hydrogen-rich monohydroperfluorooctane, alumina-treated perfluorooctane, mixtures thereof, or any suitable oxygen carrier.

Under ambient conditions when exposed to air, the PFC's will contain the same ratio of gases found in air.

Saturated or supersaturated forms of the perfluorocarbon may be made by exposing the PFC to a gas at pressure above ambient under temperature and time conditions necessary to displace other gases in the PFC with the desired gas. For example, the PFC may be saturated or supersaturated by exposing the PFC to oxygen. In some embodiments, the oxygen may be in the form of molecular oxygen, at pressures at or above ambient and under temperature and time conditions necessary to displace the other gases. The supersaturation of the PFC may be undertaken at the time of manufacture in which case the dressing will be packaged in an oxygen barrier package. Alternatively, the PFC may be added to the dressing at the time of application and the PFC may be supersaturated at the time of application to the patient.

Perfluorocarbon materials may be formed into emulsions by, for example, vortexing a dispersing agent solution with a PFC. The emulsions may be thickened by the addition of a water soluble polymer into the water phase of the emulsion. Alternatively, the emulsion may be concentrated by use of a centrifuge.

Non-limiting examples of dispersing agents include glycerols, phospholipids, lecithins, surfactants, polyoxamers, and mixtures thereof.

As would be apparent to one of ordinary skill in the art, when exposed to air under ambient conditions, the PFC's in the emulsion will contain the same ratio of gases found in air.

Saturated or supersaturated forms of the emulsions may be made by exposing the emulsion to a gas at or above ambient pressure under temperature and time conditions necessary to displace other gases in the PFC with the desired gas. For example, the PFC in the emulsion may be saturated or supersaturated by exposing the emulsion to oxygen, and the oxygen may be in the form of molecular oxygen, with pressures at or above ambient and under temperature and time conditions necessary to displace the other gases, or by simply bubbling oxygen through the emulsion.

When the device is a dressing, the dressing may be made from a non-resorbable material or a resorbable material. The oxygen carrier, as described above, may be incorporated directly into the dressing or may be a cream or gel that is applied regularly to the wound that has been treated with a dressing according to embodiments of the invention. Where the oxygen carrier has been treated to raise the proportion of oxygen then the dressing must be packaged in materials that prevent diffusion of the oxygen from the product during storage.

The implants according to embodiments of the present invention' provide a temporary scaffold for the in-growth of cells, tissues, and blood vessels to help regenerate the ECM. The delivery of oxygen helps to maintain cell health and thus facilitates and expedites the healing process. Some of the devices according to embodiments of the present invention include antibiotics to treat or prevent infection, and/or protease inhibitors to modulate protease activity in the wound. In a preferred embodiment, the device is an implant including a temporary resorbable fibrous protein scaffold, such as bone derived extra cellular matrix, that encourages the in-growth of cells, tissues, and blood vessels to assist in regenerating the ECM, and promoting healing by releasing oxygen into the chronic wound.

Oxygen carrier gels may be applied directly to a wound or may be applied to a wound contacting layer, for example, a silicone gauze (e.g., Mepitel™).

Oxygen carrier gels or emulsions may also be applied to the deep incision layers of a surgical incision prior to wound closure.

Heterotopic ossification is a problem encountered in combat related wounds where tourniquet usage has led to oxygen starvation of tissue. See for example Isaacson et al. 2014 (Isaacson et al. "Tourniquet use in combat-injured service members: a link with heterotopic ossification?" Orthopedic Research and Reviews 6 (2014): 27-31, the entire contents of which are incorporated herein by reference). Tourniquet use during Operation Enduring Freedom (OEF) and Operation Iraqi Freedom (OIF) has contributed to the high survival rate of combat-injured service members. While preservation of a life even at the potential expense of a limb should always take precedence, delayed perfusion in traumatized residual limbs may alter the proliferation, differentiation, and function of endothelial and osteoprogenitor cells. Given the synergistic relationship between angiogenesis and osteogenesis, and the influence of environmental conditions on bone formation, hypoxic conditions from tourniquets may in part explain the higher frequency of heterotopic ossification (HO) present during OIF/OEF. Accordingly, the oxygen rich dressings as disclosed in embodiments of this invention may have particular utility in the treatment of these patients as a battlefield dressing to be applied below the tourniquet.

Definitions

"Healing" as used herein generally refers to the formation of tissue at a site of a wound.

"Subject" is used herein to refer to a human or animal capable of having or acquiring chronic or acute wounds.

"Bioactive agent" is used herein to refer to therapeutic, prophylactic, and/or diagnostic agents. It includes without limitation physiologically or pharmacologically active substances that act locally or systemically in the body. "Bioactive agent" includes a single such agent and is also intended to include a plurality.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer made of two or more different monomers.

"Chronic wounds" is used herein to refer to wounds that have not healed in three months. Chronic wounds also refers to wounds caused by a chronic disease or condition in a subject.

"Acute wounds" is used herein to refer to wounds caused by a temporary incident or condition such as a burn from a fire that may not heal well due to the age, smoking habits, and/or health of the subject.

"Controlled release" as generally used herein refers to time-dependent release of bioactive agents including oxygen. It generally refers to the sustained release of bioactive agents to prolong the therapeutic action of the bioactive agent, and also to maintain the concentration of the bioactive agent in a therapeutic window.

"Extracellular matrix" or "ECM" as used herein describes a biological material derived matrix or scaffold that provides a habitat for cellular population.

"Resorbable" as used herein describes a material that is capable of being broken down in the body and eventually eliminated from the body. The terms "resorbable", "degradable", "erodible", and "absorbable" are used interchangeably in the literature in the field, with or without the prefix "bio". Herein, these terms will be used interchangeably to describe material broken down and absorbed or eliminated by the body within five years, whether degradation is due mainly to hydrolysis or mediated by metabolic processes.

Compositions

Materials have been developed to produce devices that allow the release of oxygen for the treatment of chronic wounds. Suitable devices include dressings, implants and gels or emulsions. The devices may be used for the treatment of wounds, including chronic wounds such as venous stasis ulcers, diabetic ulcers, pressure ulcers, burns, and surgical wounds.

In one embodiment, dressings may be applied to the chronic wounds, and release oxygen into the wound to stimulate healing. These dressings may subsequently be removed, and if necessary replaced with new dressings.

In another embodiment, the devices may be implants that deliver oxygen into the wound to stimulate healing. These implants are not substantially removed from the wound (although the implants may include protective barriers, for example, to control moisture or oxygen in the wound, that may be removed from the surface of the implant). In some embodiments, the implants are temporary scaffolds that are incorporated into the body, and allow cell, tissue, and blood vessel in-growth as they resorb and remodel to appropriate tissue types.

In a further aspect of the invention materials have been developed that have particular utility as scaffolds for tissue regeneration.

Scaffold Materials

The devices described herein may be produced from polymeric compositions, and/or may be produced from bone-derived collagen, which may also be described as bone-derived extra cellular matrix materials. When the devices are dressings, the devices may be made from permanent (i.e. non-resorbable) or resorbable polymeric compositions. When the devices are implants, the devices may be made from resorbable polymeric compositions, and/or may be made from the bone-derived collagen materials.

Extra Cellular Matrix Derived Scaffolds

Biological materials may be used to prepare the implants and dressings. Examples of biological materials include allogenic or xenogenic tissues such as acellular dermal matrix materials, cell-seeded dermal matrix material or cell-seeded resorbable polymers, and small intestine submucosa. In some embodiments of the present invention, bovine or human bone is demineralized and fibers formed therefrom following the methodology disclosed in US Patent Publication 2014/0314822 the entire content of which is incorporated herein by reference. Fibers may optionally be treated with a chaotropic agent such as guanidine hydrochloride to remove bone morphogenic proteins and other materials naturally occurring within the demineralized bone fiber material. Fibers from a xenogenic source may also be treated with α-galactosidase or similar materials to reduce possible immunological response. Fibers may also be treated with a plasticiser such as glycerol that renders the dried fiber flexible. The fibers may then be formed into a dressing using wet lay techniques as described in the patent. Alternatively, the entangled fibers (that have not been pre-formed into shapes) may be used as a fibrous filler to fill the wound on their own. This latter form is particularly useful for the treatment of irregular or deep wounds such as pressure sores or decubitus ulcers.

Polymers

Non-Resorbable Polymers

Permanent polymers that may be used to prepare the dressings include, but are not limited to, poly(ethylene), poly(propylene), poly(tetrafluoroethylene), poly(methacrylates), poly(methylmethacrylate), poly(ethylene-co-vinylacetate), poly(dimethylsiloxane), poly(ether-urethanes), poly (ethylene terephthalate), nylon, polyurethane, poly (sulphone), and poly(aryletherketone).

Resorbable polymers that may be used to prepare the devices (dressings or implants) include, but are not limited to, proteins, including silk, collagen (including Types I to V and mixtures thereof), collagen-based extra cellular matrix, and proteins including one or more of the following amino acids: alanine, arginine, asparagine, aspartic acid, cysteine, glutamine, glutamic acid, glycine, histidine, isoleucine, lysine, methionine, phenylalanine, proline, serine, threonine, tryptophan, tyrosine and valine; polysaccharides, including alginate, amylose, carboxymethylcellulose, cellulose, chitin, chitosan, cyclodextrin, dextran, dextrin, gelatin, gellan, glucan, hemicellulose, hyaluronic acid, derivatized hyaluronic acid, oxidized cellulose, pectin, pullulan, sepharose, xanthan and xylan; resorbable polyesters, including resorbable polyesters made from hydroxy acids (including resorbable polyesters like poly(lactides), poly(glycolides), poly(lactide-co-glycolides), poly(lactic acid), poly(glycolic acid), poly (lactic acid-co-glycolic acid), poly(dioxanones), polycaprolactones and polyesters with one or more of the following monomeric units: glycolic, lactic; trimethylene carbonate, p-dioxanone, or quadrature, -caprolactone), and resorbable polyesters made from diols and diacids; polycarbonates; tyrosine polycarbonates; polyamides (including synthetic and natural polyamides, polypeptides, and poly (amino acids)); polyesteramides; poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); biocompatible copolymers (including block copolymers or random copolymers); and hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide), or polycaprolactone or combinations thereof. Resorbable polymers also include cross-linked polymers, and include, for example, cross-linked collagen, as well as functionalized polymers. Particularly preferred resorbable polymers are resorbable polyesters.

If desired, the scaffold materials described herein may be formed from a mixture of the extracellular matrix derived and polymer fibers to produce the dressings and implants.

Figure 3:
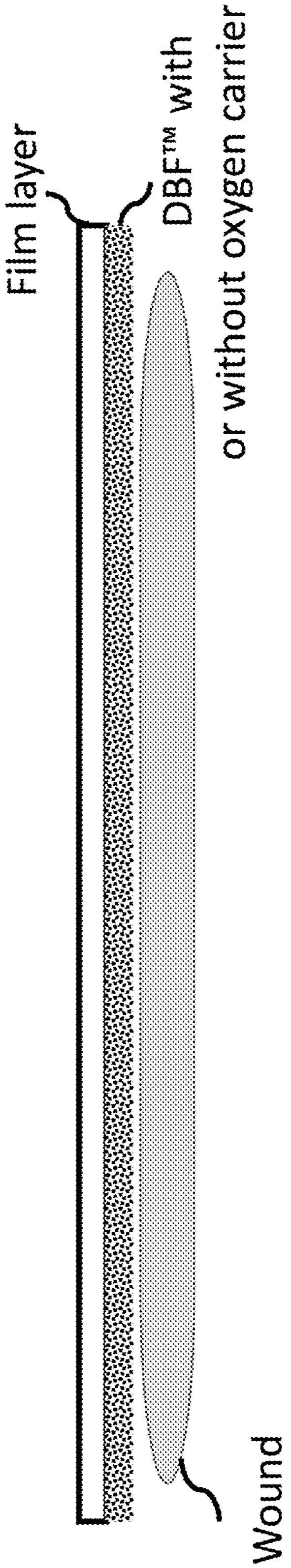
FIG. 3 shows a 4 mm thick sheet of DBF fibers with a film (e.g., polyurethane, ethylene vinyl alcohol, or silicone film) laminated to the upper surface to provide moisture control, according to embodiments of the present invention.

It should be noted that although the implants may be made from resorbable polymeric compositions, the implants may under circumstances incorporate permanent materials that do not remain in or on the body. For example, a device including a resorbable implant may also incorporate a permanent material, such as film, to control the moisture content of the wound, act as an oxygen barrier, and/or prevent infection, as depicted in FIG. 3. Although a resorbable implant is left in the wound to resorb and remodel, the permanent material is eventually removed.

Bioactive Agents

In addition to incorporating an oxygen carrier into the devices to stimulate healing, other bioactive agents may also be incorporated. These bioactive agents may be added during the preparation of the polymeric compositions, or may be added later to the devices. They may be added before, during or at the same time as the oxygen carrier. The bioactive agents may be added by using aqueous or solvent-based processes or melt-based processes.

Examples of bioactive agents that can be incorporated into the devices include, but are not limited to, angiogenic factors such as butyric acid, growth factors (e.g. VEG-F), inhibitors of matrix metalloproteinases (MMPs), agents such as retinols to aid oxygen diffusion through the tissue, antioxidants such as ascorbates to ameliorate the effects of reactive oxygen species, antibiotics (including silver particles), biofilm inhibitors, vitamins, anti-inflammatory drugs, lipids, steroids, hormones, antibodies, proteins, peptides, glycoproteins, signaling ligands, platelet rich plasma, amniotic membrane materials, anti-septic agents, analgesics, anesthetics, immunomodulatory agents, molecules that promote the formation of ECM, vascularization, and wound healing. Particularly preferred antibiotics include bacitracin, neomycin, polymixin B, zinc, fusidic acid, gentamicin, mafenide acetate, metronidazole, minocycline, mupirocin, nitrofurazone, polymixin, retapamulin, rifampin, silver particles, silver sulfadiazine, sulfacetamide, vancomycin, and combinations thereof.

Oxygenating Agents

High Oxygen Solubility Materials. Materials such as perfluorocarbons have a high inherent oxygen solubility and can act as a reservoir of oxygen within an implant.

Non-limiting examples of PFCs include perfluorodecalin, perfluorohexane, perfluoroperhydrophenanthrene, perfluorobutylamine (PFTBA or PFTBM), perfluorooctylbromide (PFOB), perfluoro-n-octane, octafluoropropane, perfluorodichlorooctane, perfluorodecalin (PFD), perfluorotripropylamine, perfluorotrimethylcyclohexane, perfluoromethyladamantane, perfluorodimethyladamantane, perfluoromethyldecaline, perfluorofluorene, diphenyldimethylsiloxane, hydrogen-rich monohydroperfluorooctane, alumina-treated perfluorooctane, mixtures thereof, or any suitable oxygen carrier.

In a further design of the device, the perfluorocarbon is incorporated into an emulsion or gel prior to coating the fibers of the dressing.

In a further design of the device, the perfluorocarbon-coated fibers include one layer of a multi-layer laminate dressing.

Perfluorocarbon materials may be formed into emulsions by, for example, vortexing a dispersing agent solution with a PFC. The emulsions may be thickened by the addition of a water soluble polymer into the water phase of the emulsion. Alternatively, the emulsion can be concentrated by use of a centrifuge.

Non-limiting examples of dispersing agents include glycerols, phospholipids, lecithins, surfactants, and polyoxamers.

Oxygen-Generating Materials. Oxygen is generated by the breakdown of materials such as Calcium Peroxide, Magnesium Peroxide, Sodium Percarbonate, or Sodium Peroxide. In some instances Hydrogen Peroxide may be an intermediate product that requires catalysis for it to break down. Catalysts such as catalase or zinc oxide can be used.

As used herein, an oxygen-generating material is also referred to as an "oxygen generator." Ideally the oxygen generating material is encapsulated in a resorbable polymer to affect control over the rate of water exposure to the oxygen generator and hence control the rate of oxygen generation.

Resorbable polymers that may be used to encapsulate the oxygen generator include, but are not limited to, proteins, including silk, collagen (including Types I to V and mixtures thereof), and proteins including one or more of the following amino acids: alanine, arginine, asparagine, aspartic acid, cysteine, glutamine, glutamic acid, glycine, histidine, isoleucine, lysine, methionine, phenylalanine, proline, serine, threonine, tryptophan, tyrosine and valine; polysaccharides, including alginate, amylose, carboxymethylcellulose, cellulose, chitin, chitosan, cyclodextrin, dextran, dextrin, gelatin, gellan, glucan, hemicellulose, hyaluronic acid, derivatized hyaluronic acid, oxidized cellulose, pectin, pullulan, sepharose, xanthan and xylan; resorbable polyesters, including resorbable polyesters made from hydroxy acids (including resorbable polyesters like poly(lactides), poly(glycolides), poly(lactide-co-glycolides), poly(lactic acid), poly(glycolic acid), poly(lactic acid-co-glycolic acid), poly(dioxanones), polycaprolactones and polyesters with one or more of the following monomeric units: glycolic, lactic; trimethylene carbonate, p-dioxanone, or .quadrature. -caprolactone), and resorbable polyesters made from diols and diacids; polycarbonates; tyrosine polycarbonates; polyamides (including synthetic and natural polyamides, polypeptides, and poly (amino acids)); polyesteramides; poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); biocompatible copolymers (including block copolymers or random copolymers); and hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide), or polycaprolactone or combinations thereof. Resorbable polymers also include cross-linked polymers, and include, for example, cross-linked collagen, as well as functionalized polymers. In some embodiments of the present invention, resorbable polymers include resorbable polyesters.

Use of a core-sheath fiber system with high load of the oxygen generator in the core allows ability to protect the system to give storage stability and to control the rate of oxygen generation. It also allows the physical properties of the fiber to be dictated by the sheath.

A porogen such as calcium carbonate may also be included in the outer sheath to also provide buffering capacity to help maintain a physiologic pH in instances where the breakdown of the oxygen generator leads to a lowering of the pH. Alternatively, buffering agents and catalysts may be formulated into the oxygen generating core material.

Wound Healing Devices and Methods of Manufacturing

Methods have been developed to produce dressings that can be used to treat wounds derived from allogenic or xenogenic bone and devices that allow the release of oxygen for the treatment of chronic wounds.

Wound Healing Devices Manufactured from Bone Derived Fibers

Fibers may be manufactured from demineralized bone using, for example, the methods disclosed in US Patent Publication 2014/0314822, the entire content of which is incorporated herein by reference. The bone is cut into struts that are then placed in dilute acid to effect demineralization. The demineralized struts are then cut using a blade to form ribbon like fibers that may be up to 4 cm in length or greater and 0.1 to 1.5 mm wide and 0.05 to 0.5 mm thick. The bone may be derived from human, bovine, porcine or other animal sources. The demineralized bone fibers (DBFs) may be derived from allogeneic or xenogenic cortical bone. For utility in soft tissue healing the demineralized bone fibers (DBFs) may be optionally treated to remove bone morphogenic proteins or other naturally present materials. A number of suitable methods exist. For example, the fibers may be treated with Guanidine Hydrochloride. Fibers from a xenogenic source may also be treated with α-galactosidase or similar materials to reduce possible immunological response. The resultant fibers can then be processed using a wet lay technique to produce a fiber dressing. Cohesion of the dressing is optionally improved by use of a heat treatment step, as disclosed in the patent application. The dressing may be optionally dried, or may be packaged and sterilized in its partially hydrated state.

Optionally the demineralized bone fibers may be dried and then rehydrated in a glycerol solution prior to the wet lay process and dried by lyophilization afterward. This renders a flexible DBF dressing in the absence of aqueous hydration.

The DBF dressing has utility as a wound dressing without further modification. It may however have a control film laminated to it. Such films could be, for example, a polyurethane film to control moisture transmission, or a silicone film to control oxygen transfer, such that it is directed towards the wound, or other materials that might facilitate application and handling of the dressing by a nurse or patient.

Oxygenating Creams and Treatments for Wound Dressings

The demineralized bone fiber dressing may optionally be further transformed to deliver oxygen by coating the fibers with a material with a high inherent oxygen solubility, such as a perfluorocarbon.

Non-limiting examples of PFCs include perfluorodecalin, perfluorohexane, perfluoroperhydrophenanthrene, perfluorobutylamine (PFTBA or PFTBM), perfluorooctylbromide (PFOB), perfluoro-n-octane, octafluoropropane, perfluorodichlorooctane, perfluorodecalin (PFD), perfluorotripropylamine, perfluorotrimethylcyclohexane, perfluoromethyladamantane, perfluorodimethyladamantane, perfluoromethyldecaline, perfluorofluorene, diphenyldimethylsiloxane, hydrogen-rich monohydroperfluorooctane, alumina-treated perfluorooctane, mixtures thereof, or any suitable oxygen carrier.

In a further design of device the perfluorocarbon is incorporated into an emulsion or gel prior to coating the fibers of the dressing. Various coating techniques may be used including dip coating, roller coating, blade over flat bed coating or other methods as any person skilled in the art would know.

Alternatively, the bone fiber dressing may optionally be further transformed to deliver oxygen by incorporating an oxygen generating material.

In some embodiments of the present invention, the oxygen generating materials are fibers that are mixed in with the DBF prior to forming the dressing by a wet lay process. In instances where water sensitive materials are used the wet lay process may use a non-aqueous solvent such as alcohol. Alternatively, other conventional textile processes such as carding, needling and/or point bonding may be used.

Wound Healing Devices Manufactured from Other Fibers

Rather than use bone derived fibers it would also be possible to use collagen fibers derived from some other source, such as bovine tendon collagen. Alternatively, fibers from any of the polymers disclosed above may be used to form a non-woven material. The fibers may be formed by electro spinning, melt, wet or solvent spinning. The non-woven material can be formed directly or by a subsequent process such as carding and needling or point bonding.

Non-woven dressings can then be coated with perfluorocarbon or perfluorocarbon gels or emulsions as described above. A film layer may also be laminated onto the dressing as described above.

Wound Healing Devices Manufactured from Foams and Sponges

The devices may contain foams, including open or reticulated cell foams, sponges, and other porous forms. These foams may be produced, for example, by phase-separation, melt-foaming, and particulate leaching methods. Alternatively, a film is frozen to precipitate the polymer, and the solvent sublimated using, for example, a lyophilizer, to form a phase separated porous polymeric foam.

The foams may also be produced by particulate leaching methods. Pore size and density may be controlled by selection of the leachable material, its size and quantity. Foams may be formed by dispersing particles in a solution of a permanent or resorbable polymer described above, wherein the particles do not dissolve in the solvent. The solvent is subsequently evaporated, and the particles leached away with a solvent that dissolves just the particles. The foams may also be produced by melt-foaming using blowing agents.

The oxygen carrier may be incorporated as part of the foam forming formulation or alternatively the foam can be infused with the oxygen carrier using a coating or impregnation process.

Wound Healing Devices Manufactured from Gels

Perfluorocarbon materials may be formed into emulsions as described above. The emulsions may be thickened by the addition of a water soluble polymer into the water phase of the emulsion. Alternatively, the emulsion may be concentrated by use of a centrifuge. The gels may be applied directly to a wound or may be applied to a wound contacting layer such as a silicone gauze such as Mepitel®.

Non-limiting examples of dispersing agents include glycerols, phospholipids, lecithins, surfactants, and polyoxymers.

Wound Healing Devices Manufactured from Laminates

Devices according to embodiments of the present invention may contain laminate structures including the materials described above. In instances where a dressing is non-resorbable and requires removal from the wound, a non-adherent wound facing layer may be utilized. The layer of the dressing incorporating the perfluorocarbon material may have a further layer laminated to form an outer surface away from the wound that provides control of moisture vapor or oxygen permeability. For oxygen permeability, the layer may have low oxygen permeability such that egress of oxygen from the dressing is directed towards the wound.

For heavily exuding wounds, a device according to embodiments of the present invention include an additional absorbent layer that is capable of being laminated onto the perfluorocarbon containing layer.

In instances where the dressing is resorbable and is designed to be incorporated into the subject (human or animal patient), the dressing may be perforated to enhance ingrowth and allow excessive exudation to egress the wound. An outer permeability controlling layer may be non-absorbable and be designed to be removed from the patient at dressing changes.

Methods of Using the Wound Healing Devices, and Their Applications

The devices according to embodiments of the present invention may be used as dressings for wound healing or they may be used as implants if at least part of the device is resorbable. In some embodiments of the present invention, the devices are used for the treatment of acute or chronic wounds. In some embodiments of the present invention, the devices are used for the treatment of chronic wounds, including venous stasis ulcers, diabetic ulcers, pressure ulcers, burns, trauma wounds, and surgical wounds.

The oxygen generating or oxygenated dressings may also be used to wrap a limb below a tourniquet following trauma, such as an explosion from an improvised explosive device (IED). For this indication, the outer part of the dressing may be laminated with an oxygen barrier polymer film to maintain the generated oxygen in the wound. Alternatively, the oxygen barrier film may be a separate bandage applied over the oxygen generating dressings.

Figure 4:
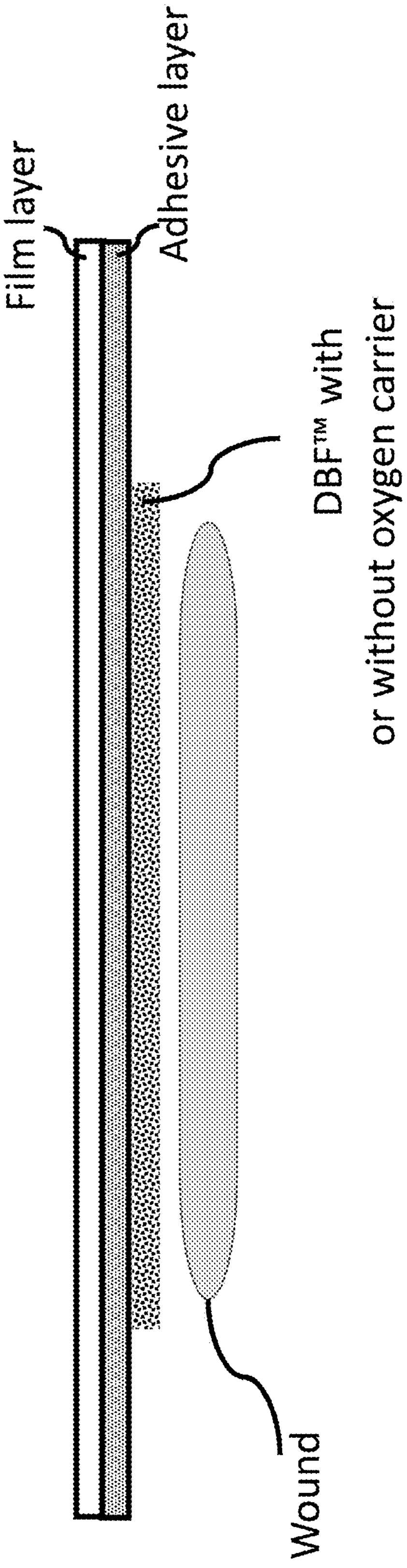
FIG. 4 shows an "island dressing" wherein a DBF sheet is covered by an adhesive coated film in which the DBF fibers are optionally coated with an oxygen carrier material, according to embodiments of the present invention.

Devices according to embodiments of the present invention are placed on or in a wound so that the oxygen may enter the wound. The devices may incorporate adhesives to help keep the device in place, and/or the devices may be held in place by another wound dressing material. For example, the devices may be held in place using compression dressings, such as when the devices are used to treat venous stasis ulcers. In another embodiment the dressing is an island on an adhesive coated film or fabric as depicted in FIG. 4.

In some embodiments of the present invention, the devices contain pores suitable for in-growth of blood vessels, cells and tissue when the devices are used as implants. In some embodiments, the devices may be left in place in the wound if they are resorbable implants, and do not need to be removed from the wound. However, these implants may also incorporate, for example, a moisture barrier or protective barrier that does need to be removed leaving behind the remainder of the implant.

In some embodiments of the present invention, the devices may also be used as dressings and removed after a period of time or replaced after a short period of time. In some embodiments, the dressing may be replaced or an additional implant ay be placed in the wound in order to maintain a delivery of oxygen to the wound.

The following Examples are presented for illustrative purposes only, and do not limit the scope or content of the present application.

EXAMPLE 1

Struts of porcine bone weighing 300 grams were placed in 3000 ml 0.6M hydrochloric acid for 6 days, with the acid changed every day. After this time the struts were demineralized, as could be confirmed by the ability to bend them by hand. They were rinsed in buffer and stored in a freezer until the next step in the process. A blade with openings 0.030"×0.050" and a tooth height of 0.012" was used to produce fibers (as shown in FIG. 1). The fibers were placed in phosphate buffered saline for 45 minutes.

Fibers weighing 150 grams were placed in 1500 ml of 4M Guanidine Hydrochloride and placed on a shaker table for 16 hours to remove the bone morphogenic proteins and other naturally present materials.

A 3 mm thick sheet of fibers was made. This was made using a wet lay technique. 45 grams of fibers were suspended in saline to form a slurry and added to a wet lay apparatus having a 4 inch by 4 inch screen. The sheet of fiber on the wet lay screen was removed and placed into a mold that pressed the sheet to a thickness of about 3 mm and then was heated at 50° C. for about an hour with a compression weight placed on top of the fiber sheet. As produced the fiber sheet is usable as a dressing.

EXAMPLE 2

Struts of porcine bone weighing 300 grams were placed in 3000 ml 0.6M hydrochloric acid for 6 days, with the acid changed every day. After this time the struts were demineralized, as could be confirmed by the ability to bend them by hand. They were rinsed in buffer and stored in a freezer until the next step in the process. A blade with openings 0.030"×0.050" and a tooth height of 0.012" was used to produce fibers. The fibers were placed in phosphate buffer for 45 minutes.

A 3 mm thick sheet of fibers was made. This was made using a wet lay technique. 45 grams of fibers were suspended in saline to form a slurry and added to a wet lay apparatus having a 4 inch by 4 inch screen. The sheet of fiber on the wet lay screen was removed and placed into a mold that pressed the sheet to a thickness of about 3 mm and then was heated at 50° C. for about an hour with a compression weight placed on top of the fiber sheet. As produced the fiber sheet is usable as a dressing.

EXAMPLE 3

Struts of rabbit bone weighing 300 grams were placed in 3000 ml 0.6M hydrochloric acid for 6 days, with the acid changed every day. After this time the struts were demineralized, as could be confirmed by the ability to bend them by hand. They were rinsed in buffer and stored in a freezer until the next step in the process. A blade with openings 0.030"×0.050" and a tooth height of 0.012" was used to produce fibers. The fibers were placed in phosphate buffer for 45 minutes.

Fibers were blotted to remove excess buffer and 1 gram placed in jars and foil pouches. Thereafter the product was sterilized using electron beam sterilization.

The fibers were hydrated and formed an entangled mass, or "putty" that could be utilized as a dressing to pack a wound.

EXAMPLE 4

A fiber dressing of Example 1 was dried overnight in a vacuum oven set at 25° C. with a 0.6 L/min air in-flow rate. The dried dressing weighed 13 grams. The dressing was placed in a tray and 8 grams of perfluorotributylamine (PFTBA, Sigma Aldrich) was applied to the dressing. A roller was used to ensure uniform distribution of the PFTBA.

EXAMPLE 5

A fiber dressing of Example 1 was dried overnight in a vacuum oven set at 25° C. with a 0.6 L/min air in-flow rate. The dried dressing weighed 13 grams. The dressing was placed in a tray and 8 grams of perfluorodecalin (PFD, Fluoromed) was applied to the dressing. A roller was used to ensure uniform distribution of the PFTBA.

EXAMPLE 6

A series of perfluorocarbon emulsions were made. Emulsifier solutions were made using Polyoxamer F127 (Sigma Aldrich) at concentrations of 0.01, 0.05 and 0.1 gram/ml. Emulsions were made using these solutions with 3 mls of perfluorodecalin and 2 mls of each of the emulsifier solutions. Mixing was achieved by rapidly passing the solutions between two syringes joined with a Luer connector. All three formulations produced emulsions.

EXAMPLE 7

A series of perfluorocarbon emulsions were made. Emulsifier solutions were made using Polyoxamer F68 (Sigma Aldrich) at concentrations of 0.01, 0.05 and 0.1 gram/ml. Emulsions were made using these solutions with 3 mls of perfluorodecalin and 2 mls of each of the emulsifier solutions. Mixing was achieved by rapidly passing the solutions between two syringes joined with a Luer connector. All three formulations produced emulsions.

EXAMPLE 8

A series of perfluorocarbon emulsions were made. Emulsifier solutions were made using Polysorbate 20 (Sigma Aldrich) at concentrations of 0.01, 0.05 and 0.1 gram/ml. Emulsions were made using these solutions with 3 mls of perfluorodecalin and 2 mls of each of the emulsifier solutions. Mixing was achieved by rapidly passing the solutions between two syringes joined with a Luer connector. All three formulations produced emulsions.

EXAMPLE 9

An emulsion of Example 6 made using Polyoxamer at 0.1 gram/ml was placed in a centrifuge. After centrifuging the emulsion had formed into a concentrated gel below a water/polyoxamer solution supernatant. The supernatant was removed to yield a concentrated perfluorocarbon gel.

EXAMPLE 10

A fiber dressing of Example 1 was dried overnight in a vacuum oven set at 25° C. with a 0.6 L/min air in-flow rate. The dried dressing weighed 13 grams. The dressing was placed in a tray and 8 grams of the gel of example 9 was applied to the dressing. A roller was used to ensure uniform distribution of the gel.

EXAMPLE 11

Figure 2:
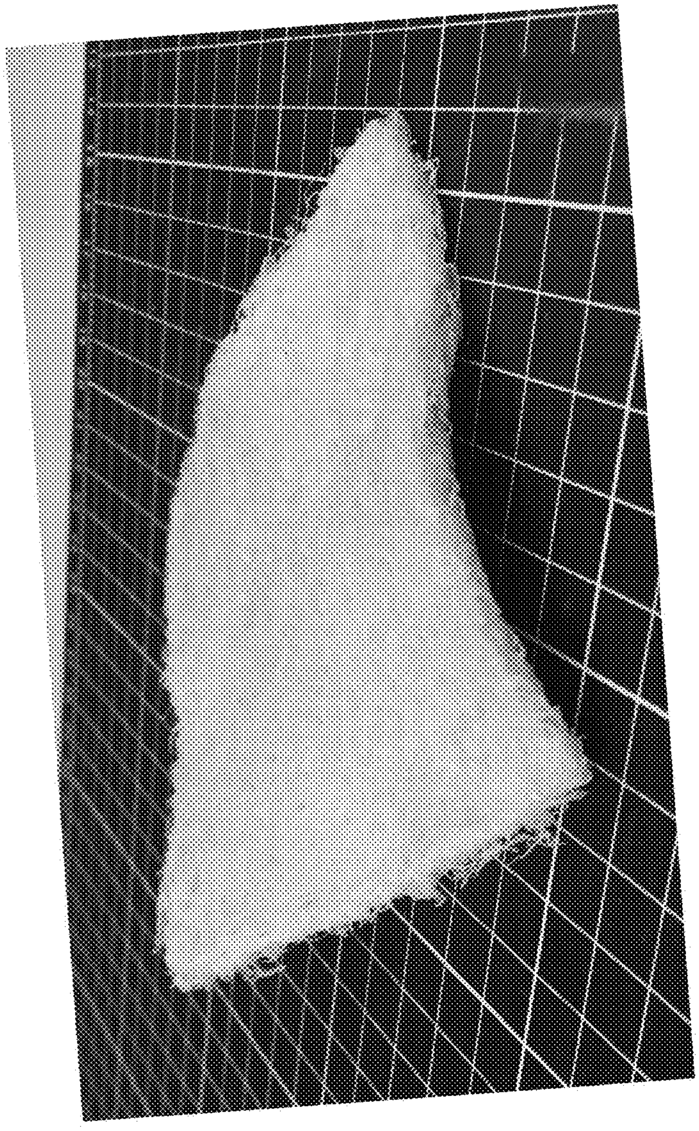
FIG. 2 shows a 4 mm thick sheet of DBF fibers according to embodiments of the present invention that may be optionally cut by the surgeon to the size of a wound and placed into it, in which the fibers are optionally coated/impregnated with an oxygen carrier material.

A series of dressings and perfluorcarbon treatments were evaluated in a porcine full thickness dermal wound model 2 cm×2 cm full thickness defects, approximately 4 mm deep were produced on the back of pigs. The following treatments were evaluated, all with a Tegaderm™ polyurethane film dressing applied to protect the treatment:

1. Porcine DBF 4 mm thick fiber dressing (as shown in FIG. 2)
2. Porcine DBF (Guanidine Hydrochloride extracted) 4 mm thick fiber dressing
3. Rabbit DBF Fiber "Putty"

Results

Wounds were examined daily and the Tegaderm dressing changed every 3 days for a total treatment time of 21 or 28 days. Histological sections were taken and processed using Haemotoxylin & Eosin (H&E), and Elastin Vierhoff Von Giessen stain. A blind histological review was undertaken by a clinical dermatopathologist.

Porcine DBFs were well integrated into full thickness porcine wounds, and normal granulation, vascularization, and new collagen deposition. As expected, re-epithelialization was slightly delayed, as the presence of the scaffold diminished wound contracture (the type of healing that occurs in porcine wounds, but not as common in human wounds). There was a significant foreign body response and some osteoid formation with osteoclast like giant cells within the healing porcine skin. The thickness of the healing dermis was better preserved with less of an indented scar than wounds that did not have scaffold present. There were more hair follicles in wounds treated with intact DBF than any other group, which suggests that signals from the DBF may have regenerative properties.

Porcine guanidine-extracted DBF integrated well into porcine wounds and normal granulation, vascularization, and new collagen deposition appeared normal. Guanidine extracted DBF resulted in less of a foreign body response than non-guanidine extracted DBF, with no osteoid formation. The thickness of the dermis was better preserved than wounds without the scaffold, but there was a slight delay in re-epithelialization, as the presence of the scaffold prevented wound contracture (the normal mechanism of healing of full thickness porcine wounds).

Rabbit DBF resulted in a robust foreign body response along with osteoid formation. Re-epithelialization was delayed and there was more granulation tissue and immature blood vessel formation, suggesting that the greater inflammatory response to the rabbit DBF was inhibiting wound healing compared to the porcine DBFs.

While the present invention has been illustrated and described with reference to certain exemplary embodiments, those of ordinary skill in the art will understand that various modifications and changes of the devices, processes, and methods described herein may be made to the described embodiments without departing from the spirit and scope of the present invention, as defined in the following claims.

The invention claimed is:

1. A fibrous composition for the treatment of a soft tissue wound, comprising:

poly(propylene), poly(ethylene), or poly(ethylene-co-vinylacetate) fibers; and an oxygen generating material and/or an oxygen carrier coated on the polypropylene, polyethylene, or poly(ethylene-co-vinylacetate) fibers, wherein the polypropylene, polyethylene, or poly(ethylene-co-vinylacetate) fibers are about 1 cm to about 30 cm in length.

2. The fibrous composition of claim 1, wherein the oxygen generating material is selected from the group consisting of calcium peroxide, magnesium peroxide, sodium percarbonate, sodium peroxide, and mixtures thereof.

3. The fibrous composition of claim 1, wherein the oxygen carrier is a perfluorocarbon selected from the group consisting of perfluorodecalin, perfluorohexane, perfluoroperhydrophenanthrene, perfluorobutylamine (PFTBA or PFTBM), perfluorooctylbromide (PFOB), perfluoro-n-octane, octafluoropropane, perfluorodichlorooctane, perfluorodecalin (PFD), perfluorotripropylamine, perfluorotrimethylcyclohexane, perfluoromethyladamantane, perfluorodimethyladamantane, perfluoromethyldecaline, perfluorofluorene, diphenyldimethylsiloxane, hydrogen-rich monohydroperfluorooctane, alumina-treated perfluorooctane, and mixtures thereof.

4. The fibrous composition of claim 1, wherein the oxygen generating material and/or the oxygen carrier are dispersed in a dispering agent forming a cream, emulsion, or gel.

5. The fibrous composition of claim 4, wherein the dispersing agent is selected from glycerols, lecithins, surfactants, polyoxymers, or combinations thereof.

6. The fibrous composition of claim 1, further comprising a bioactive agent selected from the group consisting of butyric acid, growth factors, inhibitors of matrix metalloproteinases (MMPs), retinals, antioxidants, antibiotics, biofilm inhibitors, vitamins, anti-inflammatory drugs, lipids, steroids, hormones, antibodies, proteins, peptides, glycoproteins, signaling ligands, platelet rich plasma, amniotic membrane materials, anti-septic agents, analgesics, anesthetics, immunomodulatory agents, and molecules that promote the formation of extra cellular matrix (ECM), vascularization, and wound healing.

7. The fibrous composition of claim 1, further comprising a film layer coated on the polymeric fibers.

8. A method of treating a soft-tissue wound on a subject, the method comprising:

administering the fibrous composition of claim 1 to the wound on the subject.

9. The method of claim 8, further comprising coating the fibrous composition with a cream, emulsion, or gel comprising an oxygen generating material or oxygen carrier dispersed therein, prior to, concurrent with, or after the fiber composition is administered to the wound on the subject.

* * * * *